US006662035B2

(12) United States Patent  (10) Patent No.: US 6,662,035 B2
Sochor  (45) Date of Patent: Dec. 9, 2003

(54) IMPLANTABLE LEAD CONNECTOR ASSEMBLY FOR IMPLANTABLE DEVICES AND METHODS OF USING IT

(75) Inventor: Jerzy Sochor, Sunnyvale, CA (US)

(73) Assignee: NeuroPace, Inc., Sunnyvale, CA (US)

( * ) Notice: Subject to any disclaimer, the term of this patent is extended or adjusted under 35 U.S.C. 154(b) by 0 days.

(21) Appl. No.: 09/951,234

(22) Filed: Sep. 13, 2001

(65) Prior Publication Data

US 2003/0050549 A1 Mar. 13, 2003

(51) Int. Cl.⁷ ............................. A61B 5/04; A61N 1/05
(52) U.S. Cl. ...................... 600/378; 607/116; 439/909
(58) Field of Search .......................... 600/378; 607/37, 607/38, 57, 116, 137; 439/909

(56) References Cited

U.S. PATENT DOCUMENTS

| | | | |
|---|---|---|---|
| 4,495,917 A | * | 1/1985 | Byers .......................... 607/57 |
| 4,516,820 A | * | 5/1985 | Kuzma ....................... 607/137 |
| 4,519,659 A | | 5/1985 | Shiino et al. |
| 4,712,557 A | * | 12/1987 | Harris ......................... 607/37 |
| 4,735,208 A | | 4/1988 | Wyler et al. |
| 4,850,359 A | | 7/1989 | Putz |
| 4,869,255 A | | 9/1989 | Putz |
| 4,903,702 A | | 2/1990 | Putz |
| 5,097,835 A | | 3/1992 | Putz |
| 5,215,089 A | | 6/1993 | Baker, Jr. |
| 5,237,991 A | | 8/1993 | Baker, Jr. et al. |
| 5,251,634 A | | 10/1993 | Weinberg |
| 5,351,394 A | | 10/1994 | Weinberg |
| 5,464,446 A | | 11/1995 | Dreessen et al. |
| 5,531,778 A | | 7/1996 | Maschino et al. |
| 5,560,358 A | | 10/1996 | Arnold et al. |
| 5,603,703 A | | 2/1997 | Elsberry et al. |
| 5,792,217 A | | 8/1998 | Camps et al. |
| 5,843,093 A | | 12/1998 | Howard, III |
| 5,843,148 A | | 12/1998 | Gijsbers et al. |
| 5,843,150 A | | 12/1998 | Dreessen et al. |
| 5,865,842 A | | 2/1999 | Knuth et al. |
| 5,902,236 A | | 5/1999 | Iversen |
| 5,927,277 A | | 7/1999 | Baudino et al. |
| 6,006,124 A | | 12/1999 | Fischell et al. |
| 6,011,996 A | | 1/2000 | Gielen et al. |
| 6,024,702 A | | 2/2000 | Iversen |
| 6,038,481 A | | 3/2000 | Werner et al. |
| 6,162,101 A | | 12/2000 | Fischer et al. |
| 6,163,729 A | | 12/2000 | Kuzma |
| 6,188,932 B1 | | 2/2001 | Lindegren |
| 6,201,994 B1 | | 3/2001 | Warman et al. |
| 6,321,126 B1 | * | 11/2001 | Kuzma ....................... 607/137 |
| 6,415,168 B1 | * | 7/2002 | Putz ........................... 600/378 |

* cited by examiner

Primary Examiner—Lee Cohen
(74) Attorney, Agent, or Firm—Morrison & Foerster LLP

(57) ABSTRACT

This is an implantable lead connector assembly for connecting electrode leads implanted into the brain to implantable devices. The lead connector assembly preferably includes at least one interposer for holding a lead electrode, a connector housing, a fastener, and electrical connection members that electrically link the electrode lead connections to the to pins projecting from the lead connector assembly. Electrical contact between the electrode lead and the external pins of the connector assembly is accomplished by closing the connector housing. Multiple electrical leads may be connected in this way and the electrical contacts between the connector and the electrode lead are sealed from each other and from external fluids. A method for connecting an implantable electrode lead to an implantable device using such an implantable connector is also provided.

39 Claims, 9 Drawing Sheets

IMPLANTABLE LEAD CONNECTOR ASSEMBLY FOR IMPLANTABLE DEVICES AND METHODS OF USING IT

FIELD OF THE INVENTION

This invention relates to an apparatus for connecting implantable electrode leads to an implantable device, and more particularly to an implantable connection device that may be used to connect cortical, deep brain (i.e., "depth"), or other electrode leads from a patient's brain to a device that is typically also implanted as an integrated portion of a system for detecting, monitoring, or stimulating electrical activity in a patient's brain. The invention includes methods for use of the device.

BACKGROUND

Systems for electrically monitoring and stimulating the brain are increasingly important in the medical diagnosis and treatment of various brain disorders, such as epilepsy, Parkinson's disease, sleep disorders, migraine, and psychiatric ailments. Therapeutic neurostimulatory devices may include one or more leads having at least one electrodes operatively situated in the brain or other neural tissue and linked to a signal processor for detecting neurological activity and to a pulse generator for providing electrical stimuli.

Many functional and aesthetic advantages may be achieved by implanting the signal processing and pulse generator portions of neurostimulator devices in the cranium. From a purely esthetic point of view, the electrode leads need not run along the scalp and down the neck. Connecting implanted electrodes to devices located in other regions of the body mandates that the electrode leads be lengthy. For instance, the Medtronic Activa® device uses leads that are tunneled along the neck and down the chest to the pectoral region where the neurostimulator resides. Such a pathway subjects the leads to increased risk of fatigue and to a higher susceptibility to noise from a variety of external electromagnetic sources. This inventive device assists in solving these very real problems.

One example of a system implantable beneath the scalp is found in U.S. Pat. No. 6,016,449 entitled "System for Treatment of Neurological Disorders" to Fischell, et al. (hereinafter "Fischell"). Fischell et al discloses a responsive detection and stimulation system for the early recognition and prompt treatment of a neurological event arising from neurological disorders such as epilepsy, migraine headaches, and Parkinson's disease. In Fischell et al's device, the entire implantable portion of the system for treating neurological disorders lies beneath the patient's scalp. By placing the entire system within the cranium, as opposed to extending wires into or through the neck to a control module in the chest, the probability of wire breakage due to repeated wire bending is drastically reduced. Other examples of devices implanted in the cranium for applying electrical stimulation therapies to electrodes situated at appropriate locations include cochlear implants.

Typical cranial electrode arrays are either brain surface electrode arrays or depth arrays. Brain surface electrodes often include an array of disk-shaped electrodes that are placed on the surface of the patients brain. The electrode arrays may be arranged in different formations and the number of electrodes per array may also vary. Depth electrodes are also usually small diameter leads having multiple distal electrodes on the same (or possibly branching) shaft. The major difference between the physical appearance of the two types is that the depth arrays are made up of a number of ring electrodes located distally on the lead. In either case, the proximal ends of the electrode leads may be arranged so that the those proximal contacts or termini are spaced along the shaft of the lead, electrically separated, one from the other. The physical separation of those proximal contacts is often via use of a non-conductive tubular portion, typically of the same material as the remainder of the electrode lead assembly's shaft. In turn, the lead connector assembly links the electrodes of the lead to the implantable device. It is essential that the lead connector device reliably connect each of the electrodes without functional failure.

Accordingly, it would be desirable to have an electrode lead connection device which is implantable into a patient's cranium. Such a device desirably ensures a reliable electrical connection between the electrodes and an implantable neurostimulatory or monitoring device. Furthermore, the lead connector should be easy for the surgeon to use and allow replacement of the neurostimulatory or monitoring device without having to replace the electrode leads.

SUMMARY OF THE INVENTION

This invention relates to an apparatus—an implantable lead connector assembly—for connecting implantable electrode leads to an implantable device. The invention accepts at least one electrode lead and seats it within an interposer that in turn is secured inside a connector housing that can be electrically connected to an implantable device. The entire lead connector assembly is implantable. The interposer is adapted to seat an electrode lead and allow access to all of the proximal contacts on the lead via electrical conductive members in the inventive implantable lead connector assembly. Desirably, the step of securing the connector housing in the closed position compresses electrically conductive members situated within the connector housing into contact with the electrode lead, and simultaneously compresses the seal to electrically isolate not common electrical members, resulting in a reliable electrical connection between the electrode lead and the electrical conductive members. The electrically conductive members may project through the connector housing where they can link to an implantable device, such as a signal processor or stimulator, or, alternatively, the electrically conductive members may electrically connect to passthrough pins or wires that link to the implantable device. The inventive lead connector may accommodate several lead electrodes.

The electrically conductive members, when compressible, may take differing forms.

One preferred variation of the invention includes using at least one spring contact as the compressible electrical conductive member that contacts the lead electrode and an interposer capable of accommodating the spring contacts as well as the lead electrode.

Another variation of the invention uses a fuzz button connector as the compressible electrical conductive member that contacts the lead electrode when the assembly is secured, and also an interposer capable of accommodating the fuzz button connectors as well as the electrode lead.

Another variation of the invention includes a split interposer that cooperates with other components of the inventive lead connector assembly, e.g., the connector housing that also may be split and associated connector housing seals, so that the step of securing the connector housing also seals the lead electrode within the then-joined interposer.

Still another variation of the interposer obviates the need for fuzz buttons and spring clips by use of a formed or molded interposer having regions of conductive materials generally matching the spacing of the proximal contacts on the electrode lead.

The invention further includes a method of connecting an implantable electrode lead to an implantable device. The method involves inserting an implantable electrode into a patients brain and providing an implantable lead connector assembly and an implantable device. The implantable lead connector assembly includes an interposer, a connector housing, and a fastener such that the connector housing has compressible electrical connection members that can form electrical contacts with the electrode lead when the device is secured.

DETAILED DESCRIPTION OF THE INVENTION

Figure 1:
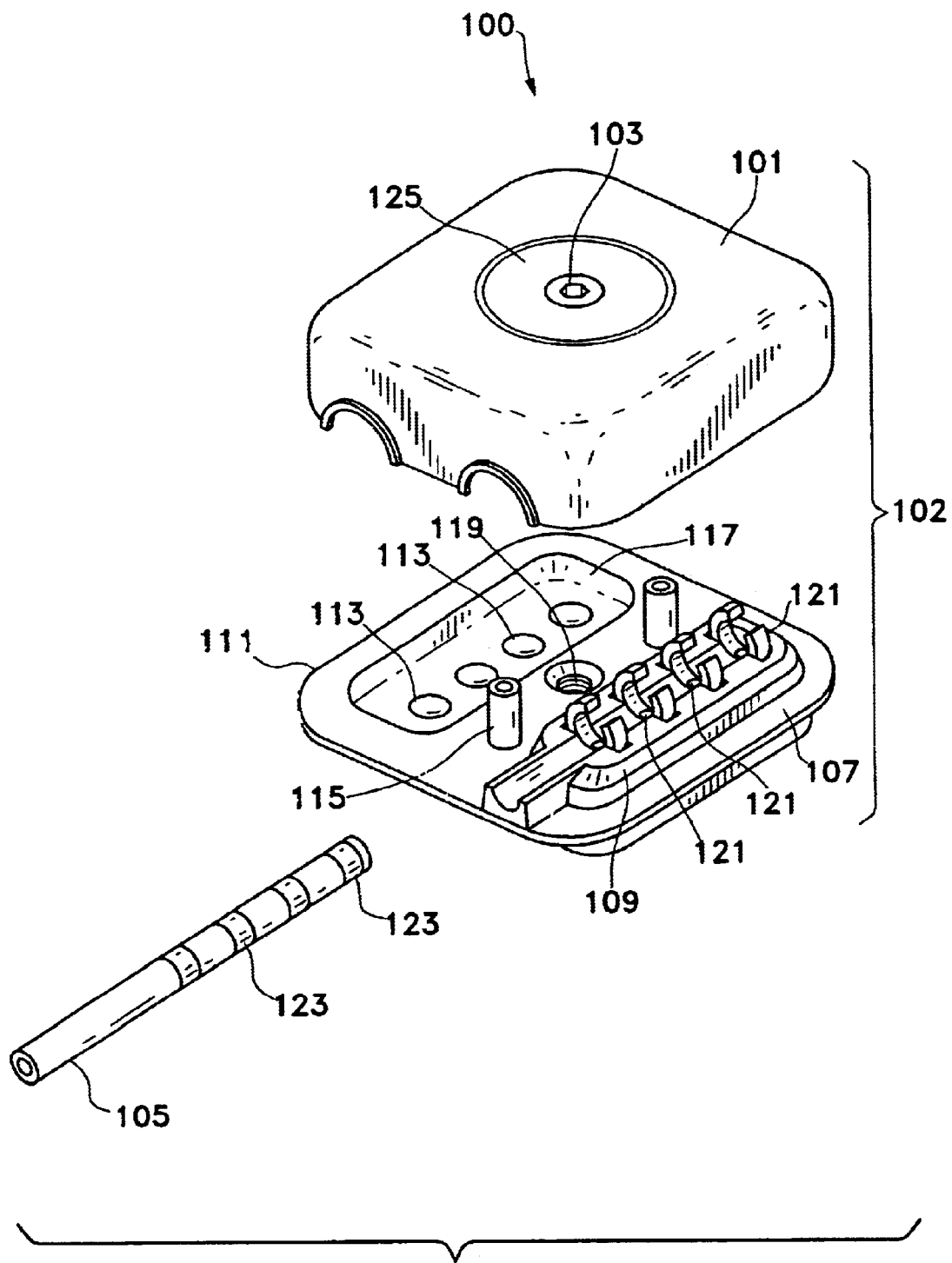
FIG. 1 is a perspective view of the electrode lead connector of the present invention shown disassembled into a clamp housing and a connector carriage with a split interposer seated therein and having a typical electrode lead.

Turning now to the drawings, FIG. 1 illustrates an implantable lead connector assembly 100 that is connectable to an electrode lead 105. The connector housing 102 of the lead connector assembly 100 desirably includes three conceptual parts: a clamp housing 101, a connector carriage 107, and an interposer or removable seal 109. Various of these functional sections may be combined or integrated as shown below, but the inventive device should have the following: a.) a functional clamp that holds the implantable lead connector assembly 100 closed and preferably simultaneously holds the various electrode leads in place while isolating the various electrical contacts, b.) an interposer or seal that accepts the proximal end of the various electrode leads and cooperatively (upon clamping or closing the inventive connector assembly) seals the various electrical contacts and "makes" the circuit with the lead contacts in such a way that the information or stimulus passing through the connector is isolated into the circuitry as intended by the designer, and c.) a connector carriage supporting the interposer, often serving as a portion of the clamping function, and desirably serving as passageway for electrical signals into and out of the attached stimulator or signal processor.

Specifically shown in FIG. 1, between the clamp housing 101 and the connector carriage 107, the electrode lead 105 is variously received by, held in place by, and positioned by an interposer or removable seal 109 that accommodates and electrically isolates electrical conductive members 121 in the connector carriage 107. In this specification, the terms "interposer," "removable seal," and "interposer seal" may be used to describe the component designated "109" in FIG. 1 because of the multiple functions performed by that component.

In any case, each of the electrical conductive members 121 make electrical contact with a corresponding lead terminus or proximal contact 123 on electrode lead 105. It is often the case in such service, that some amount of fluid (typically conductive) may be present within the confines of inventive connector assembly 102 after the device is closed and in service. The interposer 109 is to seal one electrical conductive member 121 from all non-common electrically conductive or active members thus tending to eliminate the passage of erroneous information to the attached signal processor and to certify the passage of stimulation to appropriate sectors of the brain.

In this variation of the invention, the electrical conductive members 121 pass through the connector carriage 107 and eventually project from the lead connector assembly 100 as feedthrough pins 113 (FIG. 4) where they may be linked to an implantable device such as a signal processor or stimulator mentioned elsewhere.

During assembly, the connector housing 102 (clamp housing 101 and connector carriage 107) may be joined by the fastener 103 actuating the inventive connector assembly. In this variation of the invention, engaging the fastener 103 seals the electrode lead 105 in the interposer seal 109 and presses the electrical conductive members 121 against the proximal contacts or termini 123 on electrode lead 105. This forms an electrical circuit between the electrical conductive members 121 and the electrode lead.

As shown in the Figures, the lead connector assembly 100 may receive multiple, e.g., one or two, electrode leads for connection to an implantable device. However, the invention is not so limited. The connector housing 102 may be extended or adapted to accommodate three or more electrode leads. Furthermore, although the external profile of the connector housing 102 is shown to be rectangular, the outer profiles of the clamp housing 101 and the cooperating connector carriage 107 may be of any convenient shape. To aid in attachment, the lead connector assembly's 100 shape may be adapted to fit a mounting device or a neural stimulator or signal processing device.

The lead connector assembly 100 desirably is small enough to be implanted within a patient's cranium, in a patient's cranial bone wall, or under the patient's scalp. The overall dimensions of lead connector assembly 100 will typically depend upon a variety of factors, e.g., the number of leads that the connector assembly is to accommodate, the size of the electrode leads, the size of the cranium, etc. For instance and illustrative of the tidy size of the inventive device, the lead connector assembly 100 shown in FIG. 1 has a depth of approximately 6.5 mm, and a length of approximately 15.0 mm and breadth of approximately 13.0 mm. As indicated, these dimensions are not limiting; the ultimate size and shape can vary greatly without affecting the performance of the device.

Returning to FIG. 1, the connector housing 102 is shown to be made up of at least a clamp housing 101 and a connector carriage 107. In the variation found in FIG. 1, these two components are depicted to be separable and such separability facilitates installation and replacement of electrode lead 105; however the clamp housing 101 and a connector carriage 107 may be integrated into a single element or perhaps joined by a hinge. The clamp housing can be made of a biocompatible material such as polyetheretherketone (PEEK). The interior of the clamp housing 101 holds the interposer 109 in place and therefore desirably conforms in shape to that interposer 109. This concept is discussed in greater detail below, particularly with respect to FIG. 4. Because of the many variations in the shape of the interposer 109 (see below), a variety of clamp housing designs is contemplated and clearly the interior shape of the clamp housing 101 is not limited to one having a recessed region that fits the shape of the interposer 109.

The interior of the clamp housing 101 may include one or more sealing gaskets to isolate the interior of the clamp housing 101 from external fluids after closure of the connector housing 102 by fastener 103. Preferably, however, the interposer 109 provides any required sealing. As noted above, the interposer 109 isolates each of the electrical/physical contacts occurring between the electrode lead 105 and the electrical conductive members 121 variously from each other and from the connector carriage 107. Desirably, the various gaskets and the interposer 109 are made of a biocompatible polymer, perhaps an inert elastomer such as a suitable silicone (for example, MED4950, a medical grade silicone offered by NuSil Technology of Carpinteria, Calif.). One of ordinary skill in this design art will appreciate the existence of and selection of other materials suitable for this function and for the other materials noted by example herein. A coating such as PARYLENE (polyparaxyxylene) may be applied to prevent fusion adhesion between the seal and other surfaces.

Clamp housing 101 attaches to connector carriage 107. In the same way as was the case with the clamp housing 101, the interior of the connector carriage 107 desirably supports and conforms to the interposer 109. In FIG. 1, this relationship is seen by the recessed region 117 into which the interposer 109 fits. The framework of the connector carriage 107 may be of a suitable biocompatible material, e.g., titanium. The region of the connector carriage 107 directly adjacent to the seating for the interposer 109 is the baseplate 111. Pin members 113 pass through this baseplate 111 and project from the exterior of the connector carriage 107 (see FIG. 5) where they are connectable (directly or indirectly) to an implantable device such as a signal processor, stimulator, or other device. This variation of the invention includes non-integral pins 113 passing through baseplate 111. The depicted pins 113 are fixed to the baseplate 111 but, unlike the variation discussed above, are separable from the electrical conductive members 121. Other variations include, of course, the use of electrical conductive connectors 121 that are integrated with pins 113.

Depending upon the specific design, the baseplate 111 supports or contains the electrical conductive members 121 and generally provides a sealing surface for interposer seal 109. A filtering capacitor 405 (FIG. 4) may be physically and electrically connected to baseplate 111 and to the electrical conductive members 121. The electrical conductive members 121 may also be secured to the baseplate 111 in a number of ways: for instance, by forming the baseplate 111 as a co-fired ceramic with appropriate choice of conductive regions, the electrical conductive members 121 may be made to be integral with the baseplate 111. Alternatively, as noted above, the electrical conductive members 121 may be of an assemblage containing pins 113 that are attached to baseplate 111 by, e.g., use of a biocompatible brazing material.

As shown in FIG. 1, the connection to the electrode lead 105 may include two parts: a feedthrough pin 113 and a compressible electrical connection member 121. The compressible electrical connection members 121 may be, for instance, spring contacts or fuzz button connectors and other similarly functional components. Preferably, the compressible electrical connection members 121 is a spring contact. A spring contact is an open or closed loop of a biocompatible, conductive material, such as a pure metal or an alloy (such as 80–20 Platinum-Iridium) that achieves a predictable amount of opposing force when compressed.

Alternatively, the compressible electrical connection members 121 may be fuzz buttons. Fuzz buttons may be made from a very fine diameter wire, e.g., of Pt—Ir, that is formed, much like a steel wool pad, into a shape approximating a cylinder. These forms are commercially available from Tecknit Co of Cranford, N.J. Others shapes (for example, multiple coils) and other conductive materials may also serve as compressible electrical connection members.

The feedthrough pin 113 is the portion of the electrical conductive member that extends through the baseplate 111, projects externally, and may then be attached, directly or indirectly, to the implantable device. Typically, the feedthrough pin 113 contains or is made of a suitable biocompatible, corrosion-resistant, highly conductive metal or alloy, e.g., a member of the Noble Metal group, e.g., platinum, palladium, iridium, and preferably alloys of platinum and iridium. The feedthrough pin 113 and the compressible electrical connection member 121 may, of course, be fabricated from the same conductive material or even made as a single element.

The connector carriage utilizing fuzz button connectors is shown in FIGS. 1–4. The feedthrough pins 113 and fuzz button contacts 121 are separable components of each electrical conductive member. FIGS. 6–9 show highly preferred connector carriages comprising feedthrough pins and spring contact that are welded together (by laser welding, for example).

As noted above, the lead connector assembly 100 of FIG. 1 is depicted to accept two interposer seals 109 each accommodating four electrical connections to each electrode lead 105. The number of connections 123 from a particular electrode lead 105 is not limited to four, but is set by the chosen geometry of the electrode lead 105. The lead connector assembly 100 of this invention may be configured to connect to electrode leads having a much higher density of electrodes simply by designing the location or spacing of the electrical conductive members and interposer openings to conform with the number and spacing of the various electrode termini 123.

The connector housing 102 is typically assembled by aligning the clamp housing 101 and the connector carriage 107. Ancillary assembly design aids such as alignment posts 115 on the connector carriage 107 and matching holes (not shown) in the underside of the clamp housing 101 help in aligning the connector carriage 107 to the clamp housing 101. Such alignment posts may be installed into mating holes or sockets in the connector carriage (or the connector housing) or may be formed integrally with the carriage or housing. The clamp housing 101 and connector carriage 107 may be secured together by the fastener 103 once the one or more electrode leads 105 are properly positioned in interposer 109.

The fastener 103 shown in FIG. 1 is a screw-type locking mechanism, which would desirably be pre-installed and captured in the clamp housing 101 and is adapted to lock into a threaded hole found in the connector carriage 107, sealing the electrode lead 105 in place within the interposer 109. The fastener 103 may be made out of a biocompatible polymer or of a metal such as titanium. The head of the exemplified fastener 103 shown FIG. 1 is flush with the clamp housing 101 and has a hexagonal opening for fastening and unfastening. The ability to reopen and adjust this lead connector assembly 101 is an additional benefit of this invention. Fastener 103 need not be a screw-type locking mechanism. Other fastener types—clips, Dzus-type closures, snap fasteners, integral helical joints allowing the clamp housing to twist into a closed position, clamps external to the clamp housing 101, and other closing and fastening devices having the specified function apparent to the skilled worker—are within the ambit of this disclosure.

In practice, the inventive lead connector assembly 100 may be assembled around the electrode leads 105. The proximal end (or "connector end") of the depicted electrode lead 105 has a number of proximal electrode contacts or termini 123 that are shown in FIG. 1 to be ring-type. Each of those proximal contacts 123 are in electrical contact with the distal lead electrodes implanted into the brain. The connector end of the electrode lead 105 fits into the interposer 109. The interposer 109 may be made from any suitable biocompatible insulating material, such as a silicone (for example, MED4950 silicone from NuSil Technology), that is preferably elastomeric. The interposer 109 includes an axial passageway to allow lengthwise entrance of the electrode lead 105 and openings extending generally radially to the axial passageway that typically contain the electrical connection members 121 discussed at length above. The physical and electrical contact between each proximal electrode contact 123 of the electrode lead 105 are thus made.

FIGS. 2A, 2B, and 6A–6E show variations of the interposers.

Figure 2A:
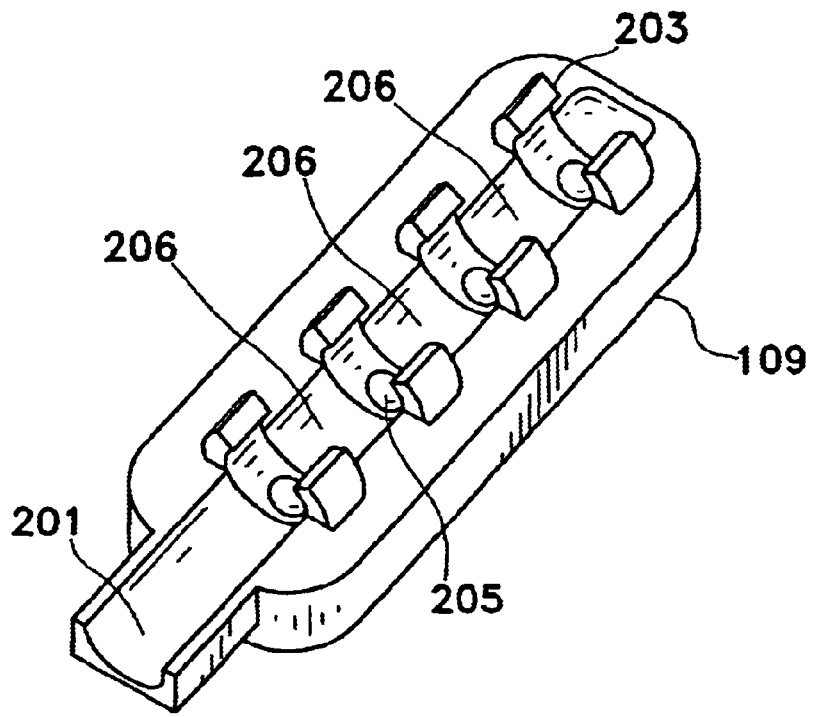
FIG. 2A is a perspective view of one variation of an interposer for holding fuzz button contacts.

In FIG. 2A, the interposer 109 has an axial passageway or channel 201 and a series of bendable, but substantially rigid clips 203 adapted to hold an electrode lead (e.g., 105 in FIG. 1) in place. This variation works especially well when the compressible electrical conductive members 205 are fuzz buttons. The interposer 109 holds electrical conductive members 205 in the openings exposed to the electrode contacts of the electrode lead. There are many variations of the overall shape of the interposer 109 of FIG. 2A that would also be effective. For example, rather than having rigid clips that are partially open to secure the electrode lead, the interposer could more completely enclose the electrode lead.

FIG. 2A also shows a number of seal surfaces 206 that conform to the spacing between the various proximal electrode contact 123 on electrode lead 105 and form a portion of the seal isolating a specific electrode contact 123 in a chamber-like opening. The corresponding portion forming the remainder of the seal wall may be seen in as the saddle-like component 108 found in the FIG. 4 depiction.

Figure 2B:
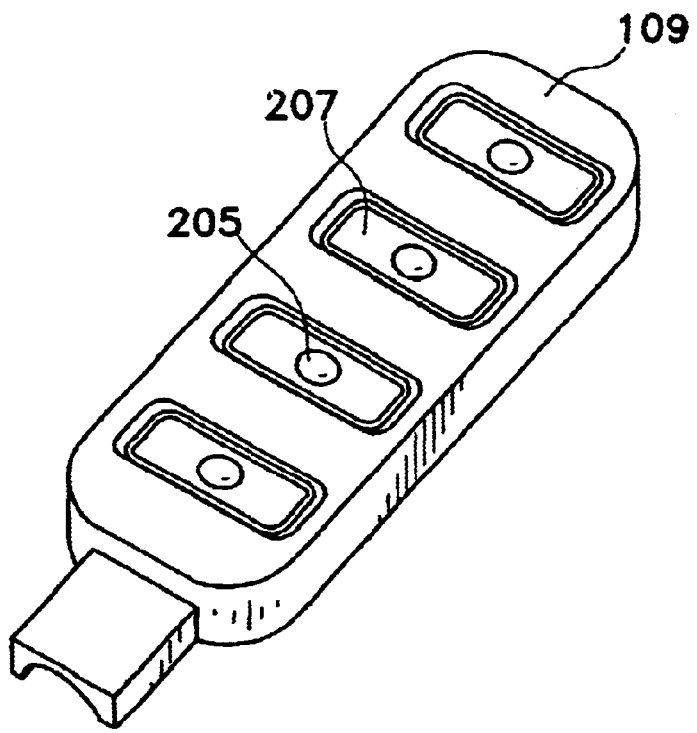
FIG. 2B is a perspective view of the interposer of 2A from the opposite side.

FIG. 2B illustrates the underside of the interposer 109 shown in FIG. 2A. This side contacts the baseplate of the connector carriage 107 as shown in FIG. 1. The compressible electrical conductive members 205 extend through the interposer 109 and are adapted to make electrical contact with the feedthrough pins 113, shown in FIG. 1. The compressible electrical conductive members 205 may be held in the openings of the interposer 109 by various structures and adhesives.

Figure 3:
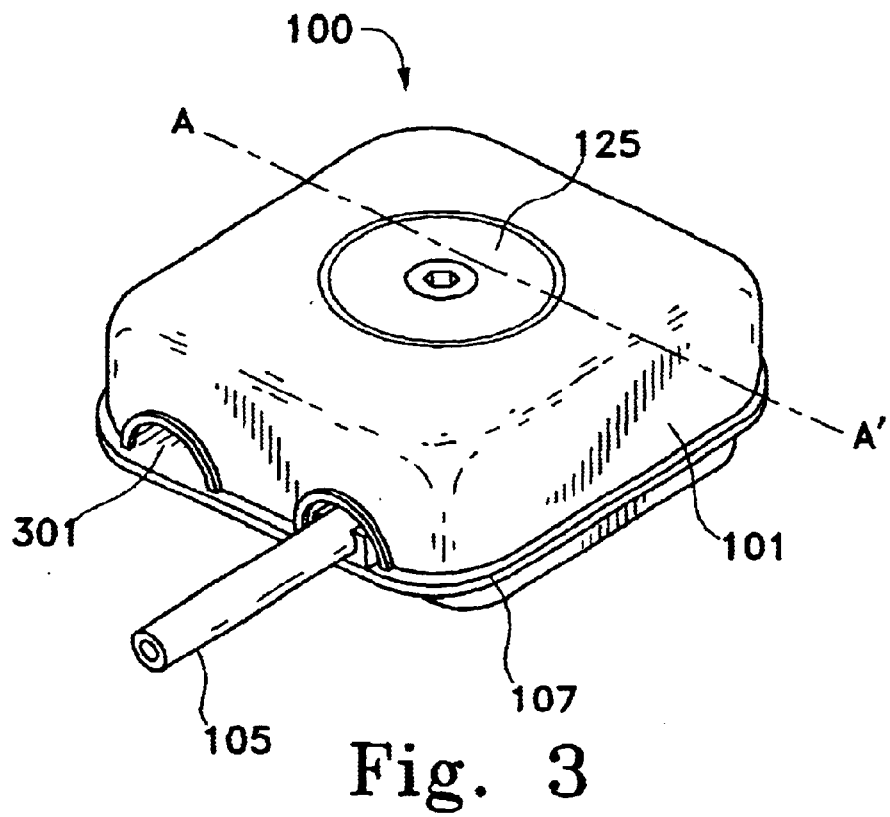
FIG. 3 is a perspective view of the fully assembled lead connector containing a single electrode lead.

FIG. 3 illustrates the assembled and sealed lead connector assembly 100. After inserting the electrode lead 105 into the interposer, the interposer is held between the clamp housing 101 and connector carriage 107. The fastener 103 is engaged, locking the clamp housing 101 to the connector carriage 107, and making electrical contacts between the electrode contact of the electrode lead and the electrical conductive members (the fuzz button connector and the feedthrough pin). The fastener put the compressible fuzz button connector in compression against the electrode lead, and also seals each contact of the electrode lead within the interposer. It is within the scope of this invention that the interposer 109 and its complementary section that fits above the portion shown in FIG. 2A within the clamp housing (all discussed elsewhere in more detail), may be detachable or removable from the connector assembly or, alternatively, those interposer seals may each be fixed (e.g., glued) respectively within clamp housing 101 and connector carriage 107. This is more thoroughly illustrated in FIG. 4.

Figure 4:
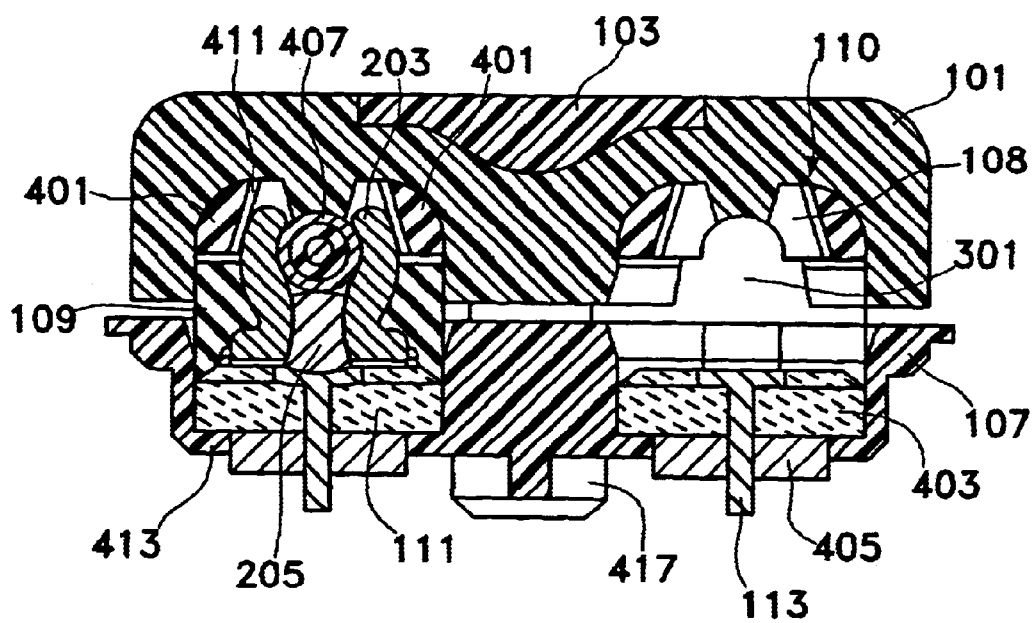
FIG. 4 is a cross-sectional view of a lead connector with fuzz button contacts taken along line A–A' of FIG. 3.

FIG. 4 shows a cross-section through the sealed lead connector assembly 100 of FIG. 3 (at section line A'–A). The electrode lead is shown sectioned though an electrode contact 407. With the fastener engaged, the electrical conductor member 205 presses against the electrode contact 407 and also against the first side of the feedthrough pin 113. The feedthrough pin 113 is shown to be slightly concave to maximize the common contact surface area between the electrical conductor member 205 and the feedthrough pin 113. This variation of the invention shows the feedthrough pin 113 to be embedded in the baseplate 111. As noted above, the baseplate 111 is seated into and is hermetically attached to the base of the connector carriage 107 and mates with the interposer 109.

In the variation shown in FIG. 4, the baseplate 111 has a ceramic layer 403 that supports and insulates the feedthrough pins 113 and a capacitive element 405 that filters transients that are transmitted through the feedthrough pins 113. The baseplate 111 is held in the connector carriage 107 and may be supported by an annular lip 413 in the bottom of the depression into which the interposer 109 resides.

The interposer 109 is held in a recessed region of the connector carriage 107, and the component rigid clips 203 hold the electrode contact in position against the electrical conductor member 205. A complementary ramp 401 is situated inside a complementary upper interposer seal 110, in turn within clamp housing 101. The complementary ramp 401 maintains the "arms" of the molded clip 203 together and against the electrode lead. The complementary upper interposer seal 110 secures the lead in place and promotes compressional contact between the electrical conductor member 205 and that electrode lead. Adjacent ramps 401 may be seen seal component 108 portion of the complementary upper interposer seal 110, mentioned above. This seal component 108, in conjunction with the seal surfaces 206 (in FIG. 2A), provides assurance that the non-common electrode contacts are fluid tight and electrically isolated from non-common adjacent electrode contacts. The surfaces variously of the seal and the interposer 109 may be provided with a coating 411 (for example, with PARYLENE) to prevent sticking or fusion adhesion amongst the seal 108, the seal surface 206 (FIG. 2A), the interposer 109, and the electrode lead. The sealed lead connector assembly 100 of FIGS. 3 and 4 are depicted to contain only one interposer and electrode lead. The space for a second lead 301 is shown unoccupied.

Figure 5:
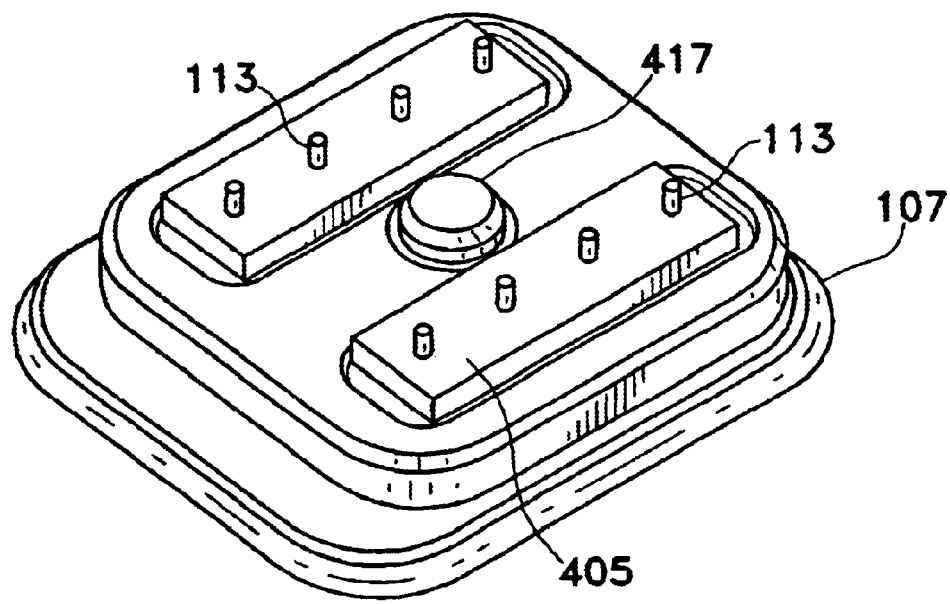
FIG. 5 is a perspective view of the opposite side of the connector carriage of FIG. 1.

FIG. 5 shows the exterior lower surface of the connector carriage 107. The exterior layer of the capacitor element 405 is shown. The most distant or second end of the feedthrough pins 113 project externally above the outer layer of the capacitor element 405 and is adapted to contact or otherwise to connect with an implantable device, such as a stimulator or signal processor. The cylindrical protrusion 417 in this variation of the invention forms a complementary section of the fastener (103 in FIG. 1) in that it houses a female threaded section when the fastener 103 is a screw or bolt. Other fastener pairs will mandate other complementary fastener components in protrusion 417. In this variation, the fastener screw threads into the connector carriage 107. A locking nut or other locking mechanism, split ring, crown washers may be employed to hold the fastener in place as eventually fastened, all as the designer sees fit. Furthermore, the shape of the protrusion 417 and of the entire outer surface of the connector carriage 107 may be designed to allow mating to or attachment of an implantable device. Of course, numerous attachment methods are suitable for the fastener, provided that the hermeticity of any attached implantable device is not compromised.

Figure 6A:
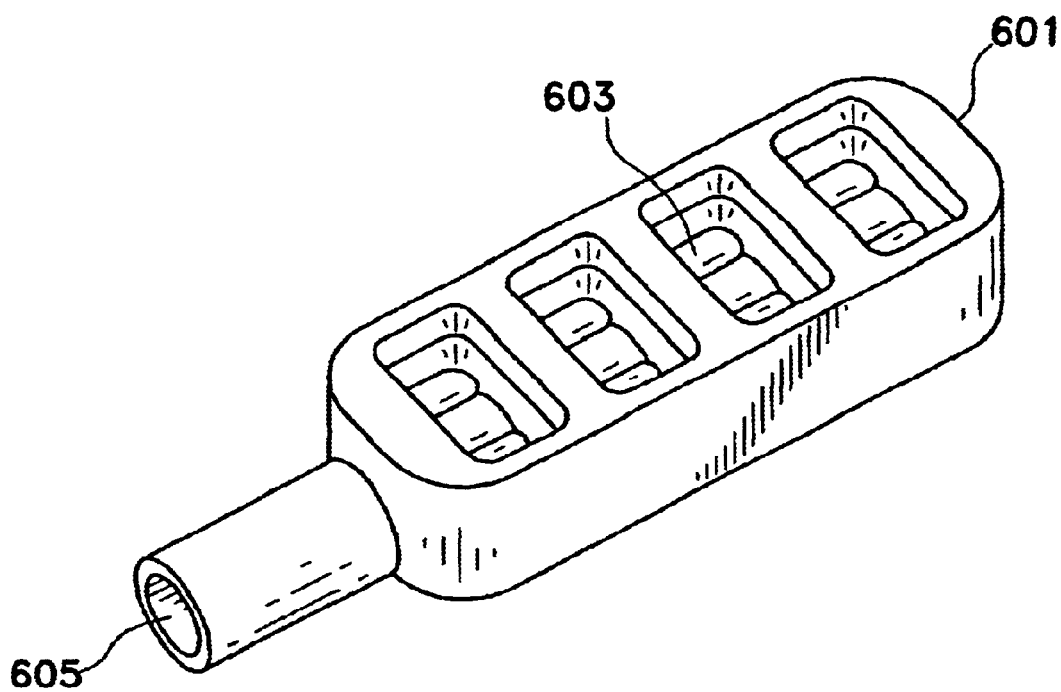
FIG. 6A is a perspective view of a variation of an interposer.

FIG. 6A shows a second, but preferred, variation of the interposer 601 that works well when the electrical connection member 603 is a spring contact. The connector end or terminal end of a electrode lead is inserted axially into the hollow channel 605. The various openings in the interposer 601 allow the spring contacts to enter the interposer 601 and form an electrical connection with the proximal contacts of the electrode lead. It is desirable that the interposer 601 be sized in such a way that when later inserted into the clamp housing (see, for instance, the depiction in FIG. 7A), the clamp housing squeezes the (preferably elastomeric) interposer 601 and, in turn, squeezes the lead and retains both in a properly aligned condition for subsequent assembly into the completed inventive housing assembly. A "properly aligned condition" means that the proximal contacts of the electrode lead are aligned in position for later electrical continuity with the complementary portions of the inventive device, e.g., the electrode lead has not undertaken any axial or longitudinal movement with respect to the to interposer. The use of the interposer to temporarily maintain various portions of the inventive device in practical subassemblies during a surgical procedure is applicable to other variations of the interposer discussed elsewhere in this specification. Indeed, it is within the scope of this invention to use other devices or assembly aids to hold various parts of the inventive device together during those surgical procedures.

Figure 6B:
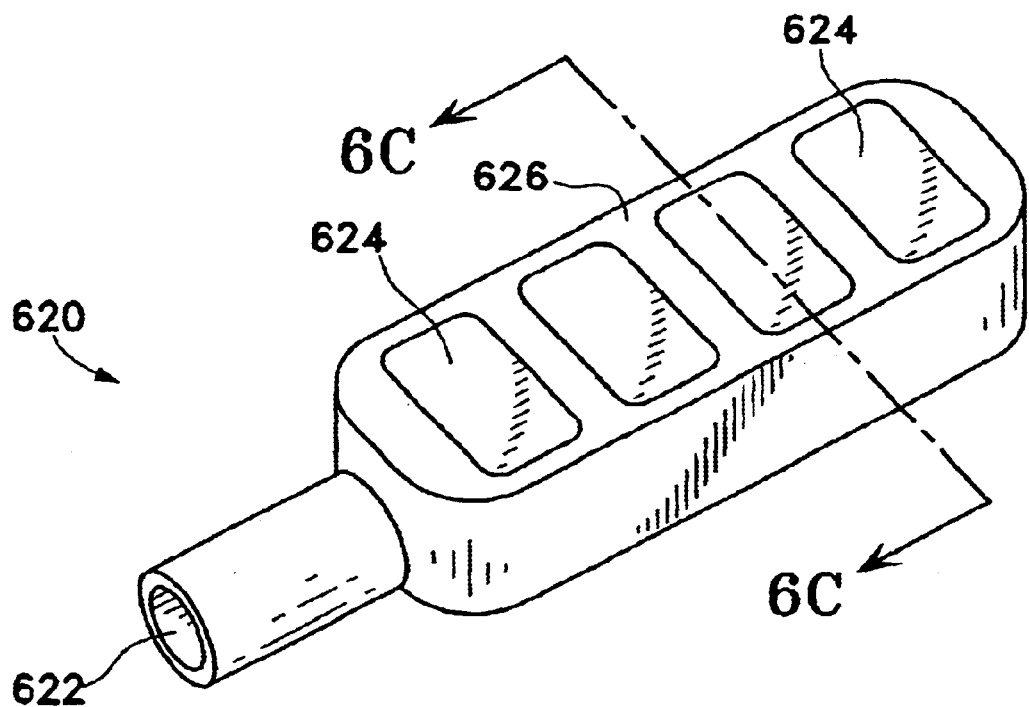
FIG. 6B is a perspective view of a variation of an interposer.

FIG. 6B shows a perspective view of a variation of the interposer 620 that is substantially closed, having only one opening, an axial passageway 622, that is adapted to accept the proximal end of an electrode lead. In this variation, the compressible electric conductor members are conductive regions 624 that match up with the spacings of the proximal contacts on an electrode lead. The interposer 620 is desirably of a selection of polymers, preferably elastomers, adapted to create the differential conductivity. The conductive regions 624 are surrounded by nonconductive areas or regions 626 that allow isolation of the current flow from or to the electrode lead to the passthrough terminals discussed elsewhere. Construction of this variation via normal polymer molding techniques should be apparent to those of ordinary skill in this art. The spring clip and fuzz buttons discussed elsewhere are not necessary in this variation. Although the axial passageway or bore 622 is shown to be smooth, other bore configurations are suitable, e.g., with projections, projecting rings, etc. The functions of contact and of sealing are to be accomplished by the structure, however. This variation fits into the connector carriage 107 in the same way as do the other variations discussed elsewhere.

Figure 6C:
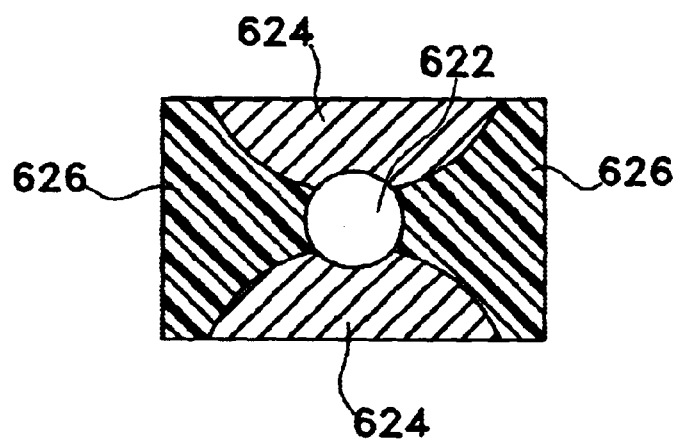
FIG. 6C is a cross section of the interposer variation shown in FIG. 6B.

FIG. 6C shows a cross-section of the FIG. 6B interposer 620. Shown are the conductive regions 624 and the surrounding non-conductive areas or regions 626 as well as the axial bore or passageway 622. The interposer 620 device is depicted to be symmetrical, although it need not be. The conductive regions 624 may be situated on but one side of the interposer 620 adjacent the passthrough terminals, although the installation in the housing must be made with more care.

Figure 6D:
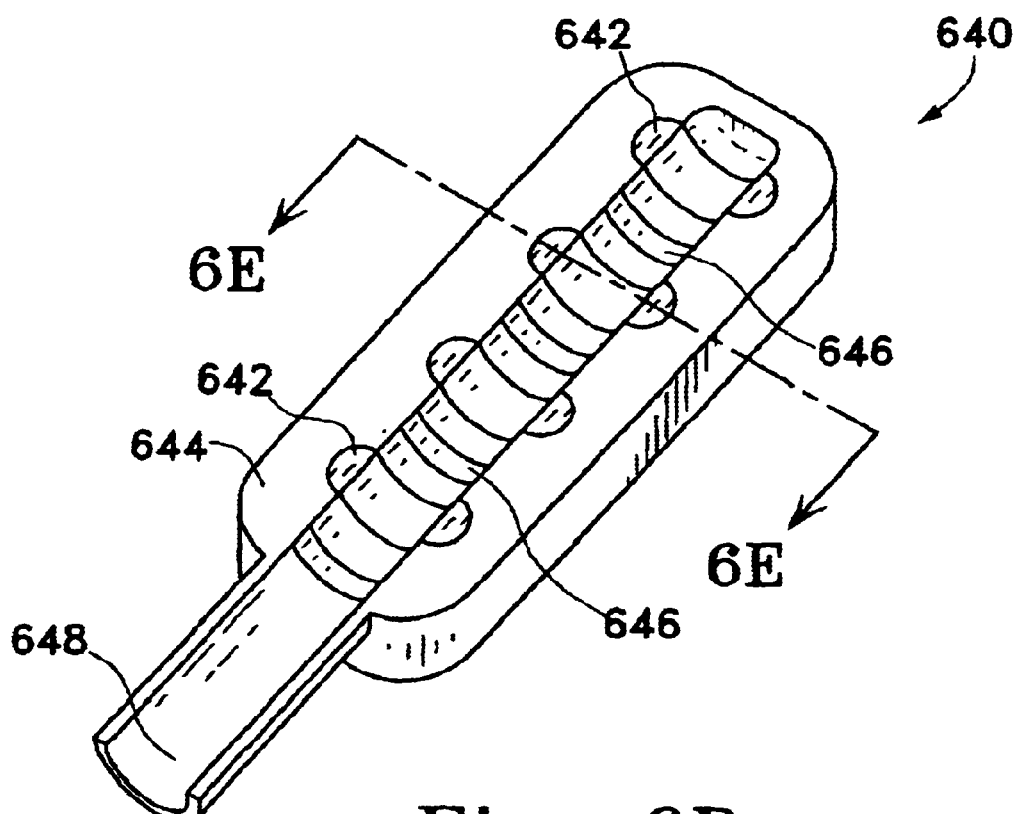
FIG. 6D is a perspective view of a variation of an interposer.

FIG. 6D shows a perspective view of another variation of the interposer 640 that comprises compressible electric conductor members that are conductive regions 642 surrounded by a non-conductive region or regions 644. This variation requires a separate cooperating upper shell to complete the seal portions shown in the axial passageway 648. The axial passageway 648 is adapted to accept the proximal end of an electrode lead. Again, the compressible electric conductor members are conductive regions 642 that match up in physical spacing with the spacings of the proximal contacts on an electrode lead. This variation fits into the connector carriage 107 in the same way as do the other variations discussed elsewhere.

Figure 6E:
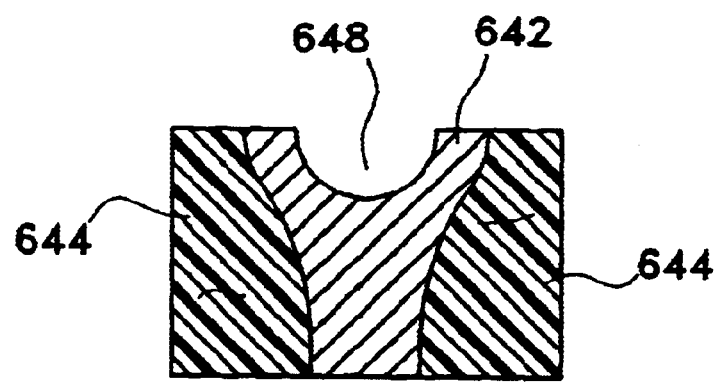
FIG. 6E is a cross section of the interposer shown in FIG. 6D.

FIG. 6E shows a cross-section of the FIG. 6D interposer 640. Shown are the conductive regions 642 and the surrounding non-conductive area or regions 644 as well as the axial bore or passageway 648.

Figure 7A:
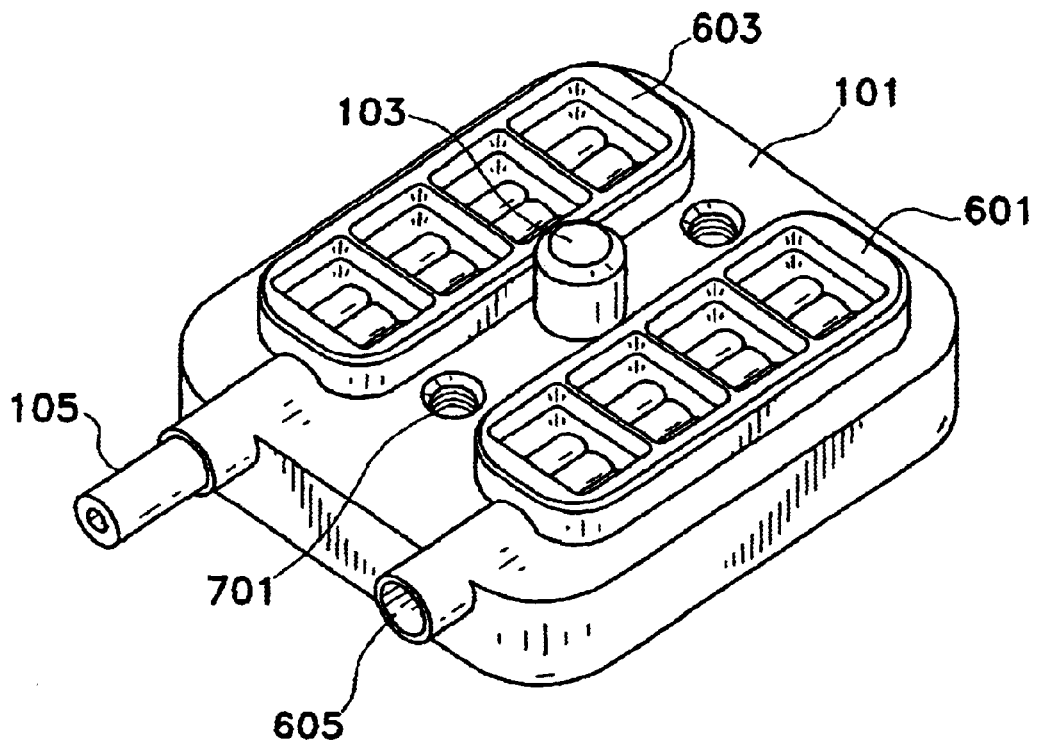
FIG. 7A is a perspective view of a clamp housing holding two interposers, one of which has an electrode lead inserted into it.
Figure 7B:
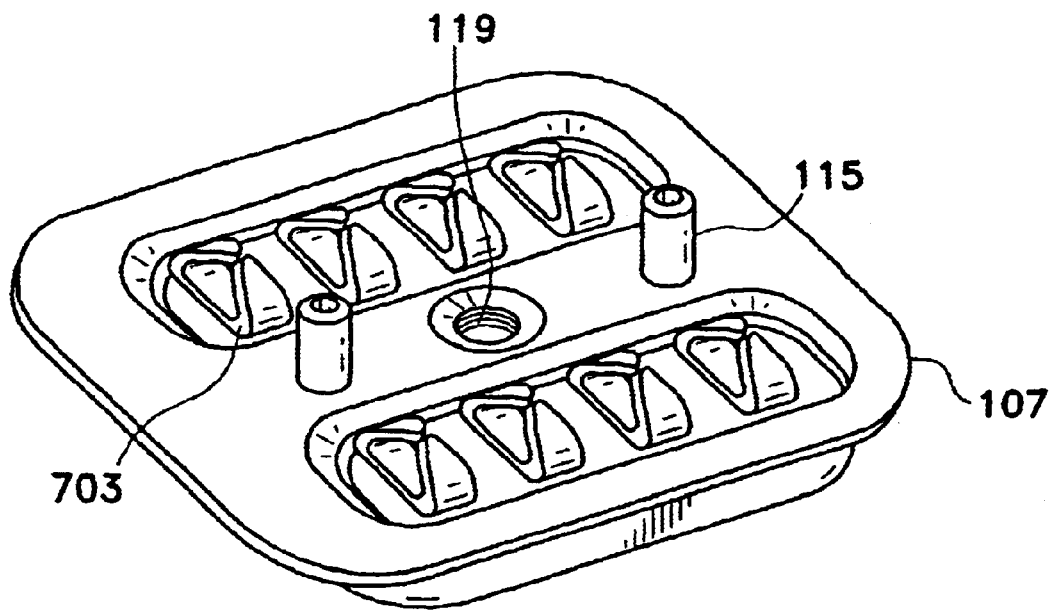
FIG. 7B is a perspective view of a variation of a connector carriage with spring contacts.

FIGS. 7A and 7B show placement of the interposer 601, after insertion of the electrode lead 105 into that interposer, in turn into the connector carriage 107 much in the same way as shown in FIGS. 1 and 4 above. The interposer 601 is held in the clamp housing 101. Alternatively, the clamp housing 101 and the interposer 601 may be integrated into a single structure. Additionally, the interposer may be preattached to the clamp housing 101. An electrode lead 105 is inserted into one of the interposers 601. The connector carriage 107 may be aligned with the clamp housing 101 using optional alignment posts 115 fitting into complementary holes 701 on the clamp housing 101. Combining the connector carriage 107 with the clamp housing 101 causes the spring electrical conductor members 703 to enter the openings in the interposer 603, and make an electrical contact with the electrode lead 105. A fastener 103 may be used to place compression on the spring electrical conductor members 703 and to lock the connector carriage 107 and the clamp housing 101 together.

In this variation of the invention, the electrical connection members (the spring contacts) 703 are welded to the proximal side of the feedthrough pins on the connector carriage (e.g., by laser spot welding). The spring contact can be made of a suitably springy, conductive, preferably inert metal or alloy (such as 80–20 Platinum-Iridium).

Figure 8:
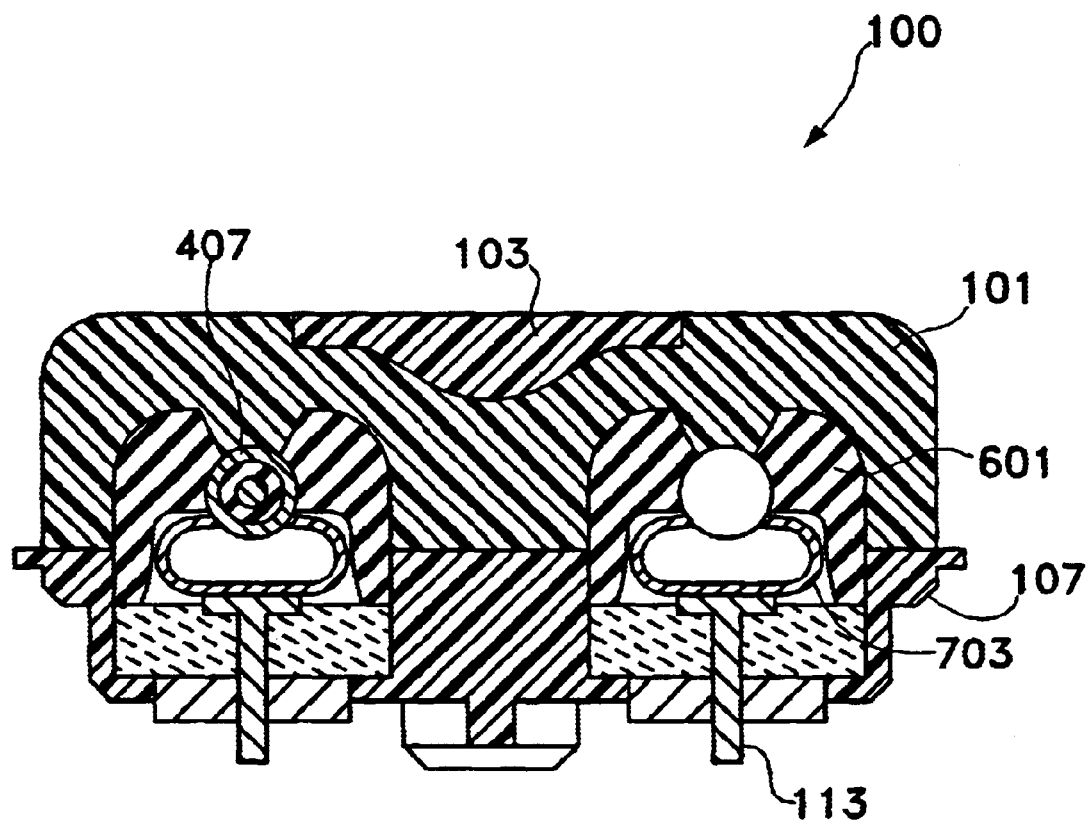
FIG. 8 is a cross-sectional view of the lead connector with spring contacts taken along line A–A' of FIG. 3.

FIG. 8 is another cross-section of the lead connector assembly 100, this time showing the electrical connection members (the spring contacts) 703 and the interposer 601 of FIGS. 6, 7A, and 7B. The electrical connection members (the spring contacts) 703 have been attached to the feedthrough pin 113, perhaps by welding, and is in electrical contact with a proximal electrode or terminus of electrode lead 407. The clamp housing 101 is locked onto the connector carriage 107 using fastener 103. This whole variation of the interposer also effectively seals the electrical contact between the electrode lead and the compressible electrical connection member from external fluids and from adjacent non-common electrical contacts and from any conductive portions of connector carriage 107.

Figure 9A:
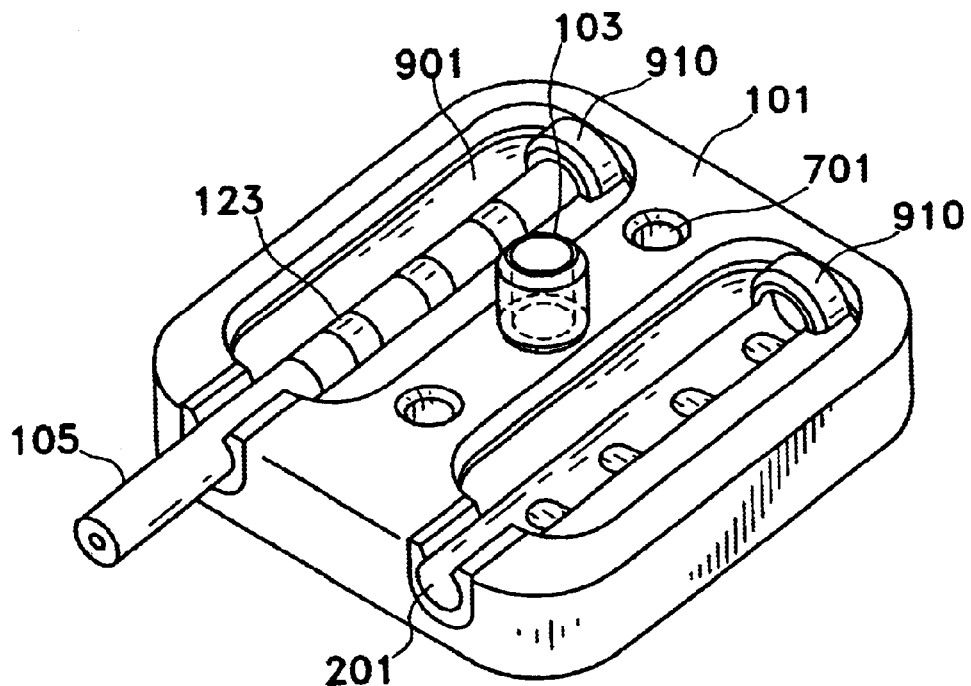
FIG. 9A is a perspective view of a clamp housing holding the top half of two split interposers, one holding an electrode lead.
Figure 9B:
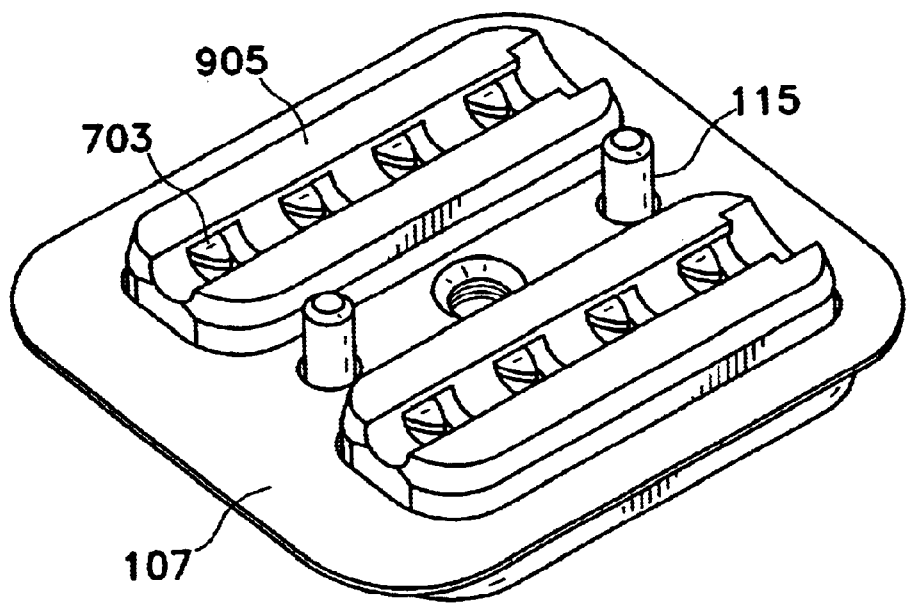
FIG. 9B is a perspective view of a variation of a connector carriage with spring contacts and the bottom halves of two split interposers.

FIGS. 9A and 9B show another variation of the interposer in which the interposer is split into an upper half 901 (see FIG. 9A) and a lower half 905 (see FIG. 9B). The upper half 901 of the interposer is set in the clamp housing 101. In FIG. 9A, the upper half 901 of the interposer may be seen residing in a recessed portion of the clamp housing 101. An electrode lead 105 is shown seated in the channel of the upper half 901. The proximal contacts or termini 123 of the electrode lead 105 are exposed in the view shown in FIG. 9A. The lower half 905 of the interposer is attached to the lead positioners 910 and has openings that fit the spring contacts 703 attached to the feedthrough pins (not seen in this view). As noted above, the interposer upper half 901 and lower half 905 may each be produced in such a way as to be affixed permanently in the respective clamp housing 101 and connector carriage 107 or they may be made in such a way as to be removable. The alignment posts 115 help join the clamp housing 101 to the connector carriage, connecting the lower half 905 of the interposer with the upper half 901 of the interposer. The alignment posts 115 in FIGS. 9A and 9B (just as in FIG. 1) project from the connector carriage into the clamp housing 101. However, alternatively, the alignment posts may just as well project from the clamp housing 101 into the connector carriage 107. Alternatively, alignment pins may be completely separate elements.

One other desirable feature is the presence of one or more lead positioners 910 such as are shown in FIG. 9A. In this depiction, the lead positioners 910 are situated in the clamp housing 101. This hooped variation of the lead positioner 910 allows a user physician to situate the lead 105 into the clamp housing 101 and be sure that that lead 105 is properly positioned so that as the clamp housing 101 is later placed onto the connector carriage 107, the proximal contacts 123 on that lead 105 are properly indexed onto the spring contacts 703. Additionally, this arrangement allows sequential assembly of the inventive device in the operating room and makes fewer the number of parts the physician must coordinate at any one time during that assembly.

Finally, fastening the fastener 103 puts the spring electrical conductor members 703 in compression against the electrode contacts and ensures electrical connections between the spring contacts 703 and the electrode contacts 123 on the electrode lead.

Although the foregoing detailed description of various variations of the present invention is set forth in some detail, the invention is not limited to those details. An implantable lead connector made or used according to the invention may differ from the disclosed variations in numerous ways. In particular, it will be appreciated that variations of the present invention may be employed in many different applications for sensing or stimulation, not just in the brain. Lead connectors according to the invention may have utility in connecting devices to lead in peripheral nerves, other portions of the body, and other applications. Rather, the invention is to cover all modifications, equivalents, and alternatives falling within the spirit of the invention as defined by the appended claims.

I claim:

1. An implantable lead connector assembly for separably, electrically connecting at least one electrode lead having at least one proximal contact to an implantable device, the lead connector assembly comprising:
   a closable connector housing having an open position adapted for accepting said at least one electrode lead and a closed position, the closable connector housing comprising seals adapted to isolate each of the at least one proximal contact in said closed position;
   a fastener adapted to maintain the connector housing in the closed position;
   at least one resilient electrical conductive member within said connector housing in electrical contact with a terminal adapted to connect said resilient electrical conductive member to said implantable device, said at least one resilient electrical conductive member further adapted to contact one of said at least one proximal contact of said at least one electrode lead, whereby changing said closable connector housing from said open position to said closed position compresses each said at least one resilient electrical conductive member contacting a proximal contact and isolates each said at least one proximal contact; and
   at least one interposer for accepting the at least one electrode lead, the at least one interposer having a sufficient number of openings exposing the at least one proximal contact of said at least one electrode lead to said at least one resilient electrical conductive member.

2. The assembly of claim 1 wherein said fastener is further adapted to change said closable connector housing from said open position to said closed position.

3. The assembly of claim 1 wherein the connector housing comprises:
   a clamp housing having an interior and an exterior, said interior of said clamp housing substantially conforming to an upper portion of at least one of said interposers; and
   a connector carriage having an interior and an exterior, said interior of said connector carriage substantially conforming to a lower portion of at least one of said interposers.

4. The assembly of claim 1 wherein said at least one interposer has conductive regions adapted substantially positionally to match the at least one proximal contact of said at least one electrode lead, wherein said at least one resilient electrical conductive member comprises said conductive regions, and said conductive regions are substantially surrounded by nonconductive regions.

5. The assembly of claim 4 further comprising a plurality of terminals, each of said plurality of terminals adapted to connect to one of said resilient electrical conductive members.

6. The assembly of claim 5 wherein each of said plurality of terminals comprises a feedthrough pin.

7. The assembly of claim 5 further comprising an insulative baseplate and wherein each of said plurality of terminals passes through said baseplate.

8. The assembly of claim 5 further comprising a filtering capacitor capacitively coupled to each of said plurality of terminals.

9. The assembly of claim 1 further comprising a plurality of said resilient electrical conductive members.

10. The assembly of claim 9 wherein said resilient electrical conductive members comprise spring contacts.

11. The assembly of claim 9 wherein said resilient electrical conductive members comprise fuzz buttons.

12. The assembly of claim 9 further comprising a plurality of terminals, each of said plurality of terminals adapted to connect to one of said resilient electrical conductive members.

13. The assembly of claim 12 wherein each of said plurality of terminals comprises a feedthrough pin.

14. The assembly of claim 12 further comprising an insulative baseplate and wherein each of said plurality of terminals passes through said baseplate.

15. The assembly of claim 12 further comprising a filtering capacitor capacitively coupled to each of said plurality of terminals.

16. An implantable lead connector assembly for separably, electrically connecting one or more implantable electrodes having at least one proximal contact to an implantable device, the lead connector assembly comprising:
   an interposer for accepting one or more electrode leads, where said interposer comprises an insulator and has openings for exposing the proximal contacts of said electrode lead and further comprising at least portions of seals adapted electrically to isolate said proximal contacts;
   a connector housing for enclosing said interposer, said connector housing having an interior and an exterior;
   a plurality of electrical conductive members passing from the interior to the exterior of said connector housing, said electrical conductive members each having a first end and a second end, such that said first ends of said electrical conductive members pass through said openings on said interposer for contacting the proximal contacts of said electrode lead and said second ends of said electrical conductive members projecting from said exterior of said connector housing; and
   a fastener adapted to compress said electrical conductive members against the proximal contacts of said electrode lead held in said interposer, forming an electrical contact.

17. The assembly of claim 16 where the connector housing is adapted to be opened and closed and wherein the fastener is further adapted to adapted to maintain said connector housing closed.

18. The assembly of claim 17 wherein said fastener is further adapted to change said connector housing from opened to closed.

19. The assembly of claim 16 wherein the connector housing comprises:
   a clamp housing having an interior and an exterior, said interior of said clamp housing substantially conforming to an upper portion of the interposer; and
   a connector carriage having an interior and an exterior, said interior of said connector carriage substantially conforming to a lower portion of the interposer.

20. The assembly of claim 16 where said plurality of electrical conductive members are resilient.

21. The assembly of claim 20 wherein said plurality of resilient electrical conductive members comprise spring contacts.

22. The assembly of claim 20 wherein said plurality of resilient electrical conductive members comprise fuzz buttons.

23. The assembly of claim 16 wherein the interior of said connector housing further comprises at least a portion of a seal that cooperatively engages with the at least portions of seals on said at least one interposer to isolate each said at least one proximal contact.

24. An implantable lead connector assembly for electrically connecting at least one implantable electrode lead each electrode lead having at least one proximal contact, to an implantable device, the lead connector assembly comprising:
   at least one interposer comprising an insulator, for holding said electrode lead, said interposer having an upper portion and a lower portion, and having openings on said lower portion for exposing said proximal contacts of said electrode lead;
   a clamp housing having an interior and an exterior, said interior of said clamp housing substantially conforming to said upper portion of at least one of said interposers;
   a plurality of compressible electrical connection members having a first and a second end, where said electrical connection members fit into said openings on said interposer such that said first ends of said electrical connection members will form electrical contacts with an electrode lead;
   a connector carriage having an interior and an exterior, said interior of said connector carriage substantially conforming to said lower portion of at least one of said interposers;
   a baseplate attached to said connector carnage;
   a plurality of electrically conductive feedthrough pins each having a first end and a second end such that said second ends of said feedthrough pins will form electrical connection to an implantable device on said exterior of said connector carriage, and said first ends of said feedthrough pins will form electrical contacts with said second ends of said electrical connection members; and
   a fastener for holding said clamp housing to said connector carriage, adapted to hold said interposer between said clamp housing and said connector carnage to make contact between said feedthrough pins and said electrode lead via said electrical connection members.

25. The assembly of claim 24 further comprising a seal interior of said clamp housing that isolates each electrode lead within said interposer between said interior of said clamp housing and said interior of said connector carriage upon engaging said fastener.

26. The assembly of claim 25 where said upper portion of said interposer further comprises clips for holding the electrode lead.

27. The assembly of claim 24 where said interior of said connector carriage further comprises at least two alignment posts adapted to fit into said alignment holes interior of said clamp housing.

28. The assembly of claim 24 where said electrical connection members are fuzz button connectors.

29. The assembly of claim 28 where said fuzz button connectors are held in said interposer by a conductive retaining layer attached to said interposer.

30. The assembly of claim 24 where said fastener is a screw passing through said clamp housing that couples with a threaded hole on said connector carriage.

31. The assembly of claim 24 where said fastener is a screw removably retained in said clamp housing.

32. The assembly of claim 24 where said baseplate further comprises at least one ceramic layer.

33. The assembly of claim 24 where said baseplate further comprises at least one filter capacitor capacitively coupled to at least one feedthrough pin.

34. The assembly of claim 24 wherein said connector carriage holds exactly two of said interposers.

35. The assembly of claim 24 wherein said electrical connection members comprise spring contacts and each of said spring contacts is attached to said first ends of each of said feedthrough pins.

36. The assembly of claim 35 wherein said spring contacts are an alloy of 80–20 Platinum-Iridium.

37. The assembly of claim 24 wherein said upper portion of said interposer is separable from said lower portion of said interposer.

38. A method of connecting an implantable electrode lead to an implantable device comprising:

provulating an implantable electrode lead;

providing an implantable device;

providing an implantable lead connector assembly, the assembly comprising an interposer having openings, a connector housing and a fastener, where the connector housing includes electrical connection members fitting within said interposer openings and that are electrically continuous with pins projecting from an external face of the connector housing.

39. The method of claim 38 further comprising the steps of:

sealing the implantable electrode lead into the interposer by activating the fastener.

* * * * *